United States Patent
Shalyaev et al.

(12) 
(10) Patent No.: US 6,441,215 B1
(45) Date of Patent: Aug. 27, 2002

(54) METHOD FOR REDUCING CARBONATE DECOMPOSITION IN REACTION MIXTURES

(75) Inventors: Kirill Vladimirovich Shalyaev, Clifton Park; Eric James Pressman, East Greenbush; John Edward Hallgren, Scotia; John Yaw Ofori, Niskayuna; Jonathan Lloyd Male, Schenectady, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/681,791

(22) Filed: Jun. 6, 2001

(51) Int. Cl.$^7$ ................................................ C07C 68/00
(52) U.S. Cl. ................................................... 558/274
(58) Field of Search ........................................ 558/274

(56) References Cited

U.S. PATENT DOCUMENTS

| | | |
|---|---|---|
| 4,187,242 A | 2/1980 | Chalk |
| 5,132,447 A | 7/1992 | King, Jr. |
| 5,142,087 A | 8/1992 | Joerg et al. |
| 5,210,269 A | 5/1993 | Di Muzio et al. |
| 5,231,210 A | 7/1993 | Joyce et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,498,789 A | 3/1996 | Takagi et al. |
| 5,502,232 A | 3/1996 | Buysch et al. |
| 5,543,547 A | 8/1996 | Iwane et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 6,114,564 A | 9/2000 | Pressman et al. |
| 6,160,155 A * | 12/2000 | Spivack et al. .............. 558/274 |
| 6,172,254 B1 | 1/2001 | Pressman et al. |
| 6,175,032 B1 * | 1/2001 | Patel et al. .................. 558/274 |
| 6,180,812 B1 | 1/2001 | Johnson et al. |
| 6,197,991 B1 | 3/2001 | Spivack et al. |

FOREIGN PATENT DOCUMENTS

| | | |
|---|---|---|
| DE | 736325 | 3/1996 |
| EP | 0071286 | 2/1983 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 10316627 | 12/1998 |
| WO | WO 00/37413 | 6/2000 |
| WO | WO 00/37419 | 6/2000 |

OTHER PUBLICATIONS 1,102,566, Patent Specification, Clark et al, Feb. 7, 1968.

* cited by examiner

Primary Examiner—Joseph K. McKane
Assistant Examiner—Golam M M Shameem
(74) Attorney, Agent, or Firm—S. Bruce Brown; Noreen C. Johnson

(57) ABSTRACT

The present invention is directed to a method for reducing the percent decomposition of an aromatic carbonate in a first reaction mixture comprising the aromatic carbonate, the method comprising the step of adding at least one decomposition-reducing additive to the first reaction mixture, so as to produce a second reaction mixture in which the percent of the aromatic carbonate present in the second reaction mixture after a predetermined amount of time is greater than the percent of the aromatic carbonate that would be present in the first reaction mixture in the absence of adding the decomposition-reducing additive, after the same predetermined amount of time.

27 Claims, No Drawings

METHOD FOR REDUCING CARBONATE DECOMPOSITION IN REACTION MIXTURES

BACKGROUND OF INVENTION

The present invention is directed to a method for reducing the percent decomposition of aromatic carbonates in reaction mixtures, and in particular a method for reducing the percent decomposition of aromatic carbonates by the addition of decomposition-reducing additives to mixtures which contain catalyst components.

Aromatic carbonates find utility as monomers in the preparation of polycarbonates. For example, a popular method of polycarbonate preparation is the melt transesterification of aromatic carbonates with bisphenols. Various methods for preparing aromatic carbonates have previously been described in the literature and are utilized by industry. A useful method for the preparation of aromatic carbonates involves the direct carbonylation of aromatic hydroxy compounds with carbon monoxide and oxygen, catalyzed by catalyst compositions typically comprising a metal catalyst, various metal co-catalysts, a salt source, and optionally an organic solvent and base. However, the desired aromatic carbonates produced by the catalytic carbonylation of aromatic hydroxy compounds are typically susceptible to decomposition in the resulting reaction mixtures due to the presence of one or more of the components of the catalyst composition or other reaction byproducts such as, but not limited to, water. Consequently, a long felt, yet unsatisfied need exists for new and improved methods for reducing the percent decomposition of aromatic carbonates in post-carbonylation reaction mixtures, so that the desired aromatic carbonate can be isolated in high yield during post reaction processing.

SUMMARY OF INVENTION

In one embodiment, the present invention is directed to a method for reducing the percent decomposition of an aromatic carbonate in a first reaction mixture comprising said aromatic carbonate, the method comprising the step of adding at least one decomposition-reducing additive to said first reaction mixture so as to produce a second reaction mixture in which the percent of said aromatic carbonate present in said second reaction mixture after a predetermined amount of time is greater than the percent of said aromatic carbonate that would be present in the first reaction mixture in the absence of adding the decomposition-reducing additive, after the same predetermined amount of time.

DETAILED DESCRIPTION

The present invention is directed in one embodiment to a method for reducing the percent decomposition of an aromatic carbonate in a first reaction mixture comprising at least one aromatic carbonate, which comprises the step of adding at least one decomposition-reducing additive to said first reaction mixture, so as to produce a second reaction mixture in which the percent of said aromatic carbonate present in said second reaction mixture after a predetermined amount of time is greater than the percent of said aromatic carbonate present in the first reaction mixture after the same predetermined amount of time. In the present context the term "decomposition" of aromatic carbonate is defined as any change in the molecular structure of the aromatic carbonate. The change in molecular structure can result from, but is not limited to, an irreversible chemical reaction between the aromatic carbonate and any other component present in the reaction mixture, resulting in the structural transformation of the aromatic carbonate into one or more molecules with lower or higher molecular weight. A typical decomposition reaction of an aromatic carbonate is a hydrolysis reaction involving water, which results in the irreversible loss of one molecule of carbon dioxide from the aromatic carbonate molecule. Another typical decomposition reaction of an aromatic carbonate is a transesterification reaction to produce a carbonate other than the desired carbonate. In the present invention, the term "reaction mixture" is defined as the total mixture of compounds which results from the carbonylation of an aromatic hydroxy compound using oxygen, carbon monoxide, and a carbonylation catalyst composition comprising at least one first metal source as a catalyst, and optionally at least one member selected from the group consisting of an inorganic co-catalyst (IOCC), a salt, a solvent, a base, and any mixtures thereof. The constituents of the reaction mixture are defined as "components" irrespective of whether a reaction between said constituents occurs. Thus the reaction mixture composition includes the components and any reaction products thereof. As used herein, the term "inorganic co-catalyst" (IOCC) includes any catalyst component that contains a metal element, which is present in the catalyst composition in addition to the first metal source. Typically, one or two IOCC's are present in the catalyst composition, and thus are present in the reaction mixture as a second metal source and a third metal source, respectively. The reaction mixture optionally further comprises unreacted aromatic hydroxy compound, and byproducts of the carbonylation reaction which typically include, but are not limited to, water, aryl ethers, poly-aromatic hydroxy compounds, and aromatic carbonates other than the desired aromatic carbonate.

In one embodiment the method of the present invention comprises the step of adding an effective amount of at least one decomposition-reducing additive to the reaction mixture. Unless otherwise noted, the term "effective amount" as used herein with respect to the decomposition-reducing additive, includes that amount of a compound capable of reducing the percent decomposition of the desired aromatic carbonate under a given set of temperature and pressure conditions. The term "decomposition-reducing additive" as used herein, is defined as any compound which, when added to the first reaction mixture containing the aromatic carbonate, reduces the percent decomposition of the aromatic carbonate in a predetermined amount of time, as compared to an identical first reaction mixture which is free of the decomposition-reducing additive. Suitable decomposition-reducing additives include, but are not limited to, compounds that comprise chelating functionalities. The term "chelating functionality" as used herein, is defined as any part of a molecule which is capable of forming at least two bonds to either a metal cation or a hydrogen cation (e.g., a proton). Typically, the bonding interactions are either ionic bonds or coordinate bonds, or combinations thereof, which are formed via heteroatoms (e.g., O, N, S, P) in the chelating functionality, thus forming a heterocyclic ring which contains at least 4 atoms including the metal cation or the hydrogen cation. A typical chelating functionality is a carboxylate functionality, which can form two coordinate bonds to a metal cation via the two carboxylate oxygen atoms. Thus in one embodiment, a decomposition-reducing additive comprises at least one chelating functionality which comprises at least one carboxylate functionality. Illustrative examples of suitable decomposition-reducing additives which contain at least one chelating functionality include, but are not limited to, oxalic acid, adipic acid, nitrilotriacetic acid, ethylenediaminetetraacetic acid, citric acid, succinic acid, malonic acid, and any mixtures thereof. In other embodiments of the present invention, a second type of suitable of decomposition-reducing additive are protic acids such as hydrobromic (HBr) acid phosphoric acid ($H_3PO_4$). For example, when the reaction mixture comprises a lead source, a suitable decomposition-reducing additive is hydrobromic acid.

The method of the present invention is suitable for an aromatic carbonate of any aromatic hydroxy compound which is convertible to a carbonate ester. For example, an aromatic carbonate formed from a monocyclic aromatic compound comprising at least one hydroxy group is suitable. Alternatively, a polycyclic aromatic compound comprising at least one hydroxy group can also be used. In one embodiment, a fused polycyclic aromatic compound, comprising at least one hydroxy group, and having from about 6 to about 30, and preferably from about 6 to about 15 carbon atoms is suitable. Illustrative examples of suitable aromatic hydroxy compounds include, but are not limited to, carbonates made from phenol, alkylphenols, alkoxyphenols, bisphenols, biphenols, and salicylic acid derivates (e.g., methyl salicylate).

The carbonylation catalyst composition present in the reaction mixture typically comprises a first metal source selected from a Group 8, 9 or 10 metal source. Typical Group 8, 9 or 10 metal sources include ruthenium sources, rhodium sources, palladium sources, osmium sources, iridium sources, platinum sources, and mixtures thereof. In one embodiment, about 1 ppm to about 1 0000 ppm of a Group 8, 9, or 10 metal source is present in the reaction mixture. In another embodiment, about 1 ppm to about 1000 ppm of a the Group 8, 9, or 10 metal source is present in the reaction mixture. In yet another embodiment of the present invention, about 1 to about 100 ppm of a Group 8, 9, or 10 metal source is present in the reaction mixture. A typical Group 8, 9, or 10 metal source is a palladium source, including palladium compounds. As used herein, with respect to metal sources, the term "compound" includes inorganic, coordination and organometallic complex compounds. The compounds are typically neutral, cationic, or anionic, depending on the charges carried by the central metal and the coordinated ligands. Other common names for these compounds include complex ions (if electrically charged), Werner complexes, and coordination complexes. The Group 8, 9, or 10 metal source is typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. Examples of suitable palladium sources include, but are not limited to, palladium sponge, palladium black, palladium deposited on carbon, palladium deposited on alumina, palladium deposited on silica, palladium halides, palladium sulfates, palladium nitrates, palladium carboxylates, palladium acetates, palladium salts of β-diketones, palladium salts of β-ketoesters, and palladium compounds containing at least one of the following ligands: carbon monoxide, amine, nitrite, nitrite, isonitrile, phosphine, phosphite, phosphate, alkoxide, alkyl, aryl, silyl or olefin.

In addition to a first metal source, the carbonylation catalyst composition present in the reaction mixture typically further comprises a second metal source selected from the group consisting of a Group 11 metal source, a Group 14 metal source and mixtures thereof. Suitable forms of Group 11 and Group 14 metal sources include, but are not limited to, elemental metals, metal oxides, and metal compounds in stable oxidation states. The compounds are typically neutral, cationic, or anionic, depending on the charges carried by the central atom and the coordinated ligands. The Group 11 and Group 14 metal sources are typically present in the reaction mixture in a homogeneous form that is substantially soluble in the reaction mixture, or alternatively in a heterogeneous form which is substantially insoluble in the reaction mixture, including metal sources supported on substrates and polymer bound metal sources. The Group 11 metal source is at least one selected from the group consisting of silver, gold and copper. Illustrative examples of copper sources include, but are not limited to, copper halides, copper alkoxides, copper aryloxides, copper nitrate, copper carboxylates, copper sulfate, and copper compounds containing at least one of the following ligands: carbon monoxide, amine, nitrite, nitrile, isonitrile, cyanide, phosphine, phosphite, phosphate, alkoxide, alkyl, aryl, silyl, olefin, β-diketone, or β-ketoester. Mixtures of Group 11 metal sources are also suitable. The Group 14 metal source is at least one selected from the group consisting of silicon, germanium, tin, and lead. Illustrative examples of lead sources include, but are not limited to, lead halides, lead oxides such as lead (II) oxide, lead carboxylates, inorganic lead salts such as lead nitrate and lead sulfate, alkoxy and aryloxy lead compounds such as lead methoxide and lead phenoxide, lead β-diketone compounds such as lead (II) 2,4-pentanedionate, organometallic lead compounds having at least one lead-carbon bond, (e.g., alkyl lead compounds such as tetraethyllead (IV)), and lead compounds containing any of the following ligands: carbon monoxide, amine, nitrite, nitrile, isonitrile, cyanide, phosphine, phosphite, phosphate, alkoxide, alkyl, aryl, silyl or olefin. Mixtures of Group 14 metal sources are also suitable. In one embodiment, about 1 equivalent to about 1000 equivalents of a second metal source, versus the amount of a Group 8, 9, or 10 metal source, is present in the reaction mixture. In another embodiment, about 1 equivalent to about 500 equivalents of a second metal source, versus the amount of a Group 8, 9, or 10 metal source, is present in the reaction mixture. In yet another embodiment of the present invention, about 1 equivalent to about 100 equivalents of a second metal source, versus the amount of a Group 8, 9, or 10 metal source, is present in the reaction mixture.

In one embodiment of the present invention, in addition to the first and second metal sources, the carbonylation catalyst composition present in the reaction mixture also comprises a third metal source. The third metal source is typically present in the reaction mixture in a homogeneous form that is substantially soluble in the reaction mixture or in a heterogeneous form which is substantially insoluble in the reaction mixture, including, supported or polymer bound species. For example, in one embodiment of the present invention, in addition to the first metal source, the carbonylation catalyst composition further comprises both a Group 11 metal source and a Group 14 metal source, which are present in the reaction mixture as the second metal source and third metal source, respectively. In another embodiment of the present invention, the reaction mixture further comprises a third metal source which is typically is at least one Group 4 metal source. Suitable Group 4 metal sources include zirconium sources, hafnium sources, and titanium sources. Illustrative examples of titanium sources include, but are not limited to, titanium halides, titanyl oxides, titanium alkoxides, titanium aryloxides, titanium nitrates, titanium carboxylates, titanium sulfates, and titanium compounds containing at least one of the following ligands: carbon monoxide, amine, nitrite, nitrate nitrite, isonitrile, cyanide, phosphine, phosphite, phosphate, alkoxide, alkyl, aryl, silyl, olefin, β-diketone, or β-ketoester. Mixtures of Group 4 metal sources are also suitable. In one embodiment, about 1 equivalent to about 1000 equivalents of a third metal source, versus the amount of a Group 8, 9, or 10 metal source, is present in the reaction mixture. In another embodiment, about 1 equivalent to about 500 equivalents of a third metal source, versus the amount of a Group 8, 9, or 10 metal source, is present in the reaction mixture. In yet another embodiment of the present invention, about 1 equivalent to about 100 equivalents of a third metal source, versus the amount of a Group 8, 9, or 10 metal source, is present in the reaction mixture.

The reaction mixture optionally further comprises at least one salt, which is present as part of the carbonylation catalyst composition. Illustrative examples of salt sources present in the reaction mixture include, but are not limited to, carboxylates, acetates, benzoates, nitrates, phosphates, phosphites, tetraarylborate, sulfates, alkylsulfonates, arylsulfonates, alkali halides, alkaline-earth halides, guanidinium halides, and onium halides (e.g., ammonium halides, phosphonium halides and sulfonium halides). Typical onium cations contain organic residues, which include C1–C20 alkyl, C6–C10 aryl, or alkyl-aryl combinations thereof. In one embodiment, about 1 equivalent to about 100000 equivalents of a salt source, versus the amount of a Group 8, 9, or 10 metal source, is present in the reaction mixture. In another embodiment, about 1 equivalent to about 10000 equivalents of a salt source, versus the amount of a Group 8, 9, or 10 metal source, is present in the reaction mixture. In yet another embodiment of the present invention, about 1 equivalent to about 1000 equivalents of a salt source, versus the amount of a Group 8, 9, or 10 metal source, is present in the reaction mixture.

The reaction mixture optionally further comprises at least one organic solvent. Suitable organic solvents for the present invention include polyethers (e.g. compounds containing two or more C—O—C linkages). The polyether is typically an aliphatic or mixed aliphatic-aromatic polyether. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Suitable aliphatic polyethers include, but are not limited to, diethylene glycol dialkyl ethers such as diethylene glycol dimethyl ether (hereinafter "diglyme"), triethylene glycol dialkyl ethers such as triethylene glycol dimethyl ether (hereinafter "triglyme"), tetraethylene glycol dialkyl ethers such as tetraethylene glycol dimethyl ether (hereinafter "tetraglyme"), polyethylene glycol dialkyl ethers such as polyethylene glycol dimethyl ether and crown ethers such as 12-crown-4 (1,4,7,10-tetraoxacyclododecane), 15-crown-5 (1,4,7,10,13-pentaoxacyclopentadecane) and 18-crown-6 (1,4,7,10,13,16-hexaoxacyclooctadecane). Illustrative examples of mixed aliphatic-aromatic polyethers include, but are not limited to, diethylene glycol diphenyl ether and benzo-18-crown-6. Mixtures of polyethers are also suitable. Another example of a suitable organic solvent for the present invention is a nitrile solvent. Suitable nitrile solvents for the present invention include, but are not limited to, C2–C8 aliphatic or C7–C10 aromatic mononitriles or dinitriles. Illustrative mononitriles include, but are not limited to, acetonitrile, propionitrile, and benzonitrile. Illustrative dinitriles include, but are not limited to, succinonitrile, adiponitrile, and benzodinitrile. A further example of a suitable organic solvent for the present invention is a carboxylic acid amide. Typically, fully substituted aliphatic, fully substituted aromatic or fully substituted heterocyclic amides (containing no NH groups including the amide nitrogen) are used. Illustrative examples of carboxylic acid amides include, but are not limited to, dimethylformamide, dimethylacetamide (hereinafter sometimes "DMA"), dimethylbenzamide and N-methylpyrrolidinone (NMP). In yet another embodiment of the present invention, the organic solvent present in the reaction mixture is an aliphatic, aromatic or heterocyclic sulfone. Illustrative examples of suitable sulfones include, but are not limited to, dimethyl sulfone, diethyl sulfone, diphenyl sulfone and sulfolane (tetrahydrothiophene-1,1-dioxide). In one embodiment of the present invention, about 1% to about 60% by volume of organic solvent, based on the total volume of the reaction mixture, is used. In another embodiment of the present invention, about 1% to about 20% by volume of organic solvent, based on the total volume of the reaction mixture is used. In yet another embodiment of the present invention, about 1% to about 10% by volume of organic solvent, based on the total volume of the reaction mixture is used.

In one embodiment of the present invention, the reaction mixture further comprises at least one base source. Suitable base sources include, but are not limited to, basic oxides, hydroxides, mono or polyalkoxides with linear or branched alkyl chains having from about 1 to about 30 carbon atoms, and aryloxides including monocyclic, polycyclic or fused polycyclic aromatic monohydroxy or polyhydroxy compounds having from about 6 to about 30, and preferably from about 6 to about 15 carbon atoms. Examples of suitable bases include, but are not limited to, sodium hydroxide, lithium hydroxide, potassium hydroxide, tetraalkylammonium hydroxides (e.g. tetramethylammonium hydroxide, tetraethylammonium hydroxide, methyltributylammonium hydroxide and tetrabutylammonium hydroxide) sodium phenoxide, lithium phenoxide, potassium phenoxide, and tetraalkylammonium phenoxides (e.g. tetramethylammonium phenoxide, tetraethylammonium phenoxide, methyltributylammonium phenoxide and tetrabutylammonium phenoxide). A second class of suitable bases includes tertiary amines, with organic residues comprising either alkyl residues having from about 1 to about 20 carbon atoms, or aryl residues having from about 6 to about 30, and preferably from about 6 to about 15 carbon atoms, or alkyl-aryl combinations thereof. In one embodiment, an example of a tertiary amine base is triethyl amine. In one embodiment, about 1 equivalent to about 10000 equivalents of a base source, versus the amount of a Group 8, 9, or 10 metal source, is present in the reaction mixture. In another embodiment, about 1 equivalent to about 1000 equivalents of a base source, versus the amount of a Group 8, 9, or 10 metal source, is present in the reaction mixture. In yet another embodiment of the present invention, about 1 equivalent to about 500 equivalents of a base source, versus the amount of a Group 8, 9, or 10 metal source, is present in the reaction mixture.

The temperature of the reaction mixture of the present invention to which the decomposition-reducing additive is added is typically about 50° C. to about 220° C. In one embodiment the temperature of the reaction mixture, to which the decomposition-reducing additive is added to, is about 70° C. to about 120° C. In another embodiment, the temperature of the reaction mixture, to which the decomposition-reducing additive is added to, is about 160° C. to about 210° C.

The pressure of the reaction mixture of the present invention to which the decomposition-reducing additive is added is typically about $1.3\times10^{-4}$ MPa to about 10 MPa. In one embodiment the pressure of the reaction mixture, to which the decomposition-reducing additive is added to, is about $1.3\times10^{-4}$ MPa to about 1 MPa. In another embodiment, the pressure of the reaction mixture, to which the decomposition-reducing additive is added to, is about $1.3\times10^{-4}$ MPa to about 0.1 MPa.

The following examples are included to provide additional guidance to those skilled in the art in practicing the claimed invention. The examples provided are merely representative of the present invention. Accordingly, the following examples are not intended to limit the invention, as defined in the appended claims, in any manner. The examples listed in tables 1–4 show the effect of the various decomposition-reducing additives in reducing the percent decomposition of diphenyl carbonate (DPC), in post carbonylation reaction mixtures comprising various carbonylation catalyst compositions. A metric used in the following examples to demonstrate the utility of the invention is the "% Decomposition of DPC", which is a measure of the amount of DPC remaining in a given reaction mixture, after the decomposition-reducing additive has been added to the reaction mixture, and the reaction mixture has been heated to a specified temperature for a predetermined amount of time. Comparative examples (e.g., examples C1, C2, C7, C12, C17, C21, C24, C28) treated under the same conditions as the illustrative examples, but in which no decomposition-reducing additive was added to the reaction mixture, are provided for each type of reaction mixture. In addition to DPC, all reaction mixtures in the following examples typically comprise phenol, biphenols, halophenols, polyhydroxyaromatic oligomers, other aromatic carbonates besides DPC, and water. Tables 1–4 list the specific components of the carbonylation catalyst composition present in the various reaction mixtures. The palladium source was originally added to the various reaction mixtures as palladium(II) 2,4-pentanedionate (Pd). The other components of the carbonylation catalyst compositions are present in quantities reported as equivalents versus palladium (eq. vs. Pd), and were originally added to the reaction mixtures as copper (II) 2,4-pentanedionate (Cu); lead(II) oxide (Pb); titanium (IV) oxide 2,4-pentanedionate (Ti); sodium bromide (NaBr); tetraethyl ammonium bromide (TEAB); sodium chloride (NaCl); tetraethyl ammonium chloride (TEAC); sodium hydroxide (NaOH); and tetraglyme (TG).

The reaction mixture used in example 1 and comparative example C1 was generated and treated as follows: a 1 gallon autoclave, equipped with a stirrer, a condenser, and gas inlet and exit ports capable of continuous gas feed at constant pressure, was charged with a first solution comprising phenol (1250 g; 13.3 mol) and lead(II) oxide (6 g; 26.9 mmol) and heated to 60° C. while stirring. To the stirred first solution was added a second solution of phenol (1250 g; 13.3 mol) and tetraethyl ammonium bromide (55 g; 262 mmol), preheated to 60° C. Finally, a third solution of phenol (500 g; 5.3 mol) and palladium (II) 2,4-pentanedionate (0.150 g; 0.493 mmol), preheated to 60° C., was added to the first solution, and the reactor was sealed and pressurized to 9.3 MPa with 1150 standard litres per hour (SLPH) of carbon monoxide and 81 SLPH of oxygen. The reaction temperature was elevated to 100° C. and maintained for 2.5 hours with stirring. The reactor was then cooled to 50° C., and depressurized to atmospheric pressure. A continuous sample (9–11 grams/minute) from this reaction mixture was fed into a glass bottom wiped-film evaporator with a glass column heated to 210° C. surface temperature, and subjected to low pressure (16–18 mm Hg) distillation conditions in order to demonstrate the effect of an 48% aqueous hydrobromic acid solution (HBr) on reducing the percent decomposition of DPC under the effects of temperature and increasing DPC concentration. Reaction mixtures were analyzed by high performance liquid chromatography (HPLC).

Examples 2–41 and the remaining comparative examples show the effect of various additives (HBr; ethylenediaminetetraacetic acid (EDTA); oxalic acid (OA); nitrilotriactic acid (NTA); adipic acid (AA), citric acid (CA), malonic acid (MA); phosphoric acid (PA); succinic acid (SA)) on reducing the percent decomposition of DPC under static conditions. A representative reaction mixture (e.g., examples C24, 24–27) was generated as follows: a 450 mL Hastelloy-C autoclave was charged with phenol (64 g; 681 mmol), palladium (II) acetylacetonoate (Pd; 0.00281 g; 0.0092 mmol; 15 ppm), copper (II) 2,4-pentanedionate (Cu; 0.0121 g; 0.0462 mmol; 5 eq. vs. palladium), titanium(IV) oxide 2,4-pentanedionate (Ti; 0.0362 g; 0.1381 mmol; 15 eq. vs. palladium), tetraethyl ammonium bromide (TEAB; 1.5134 g; 7.2066 mmol; 780 eq. vs. palladium), and sodium hydroxide ( NaOH; 0.01476 g; 3.6900 mmol; 400 eq. vs. palladium). Molecular sieves (1/16" pellets, 3 Å, 30 g) were placed in a perforated Teflon® basket inside the reactor, and the reactor was sealed and pressurized to 10.3 MPa with a premixed gas supply comprising about 8.9% oxygen in reagent grade carbon monoxide. The contents of the reactor were heated to about 100° C., and stirred for about 2 hours, after which time the reactor was cooled to room temperature and depressurized. A similar procedure was followed to prepare the other reaction mixtures utilized in the other comparative examples and examples comprising the specific carbonylation catalyst components described in tables 2–5. The decomposition experiments involving the decomposition-reducing additives were performed in glass vials charged with about 50 microliter aliquots, which were about 67% by volume of a specific reaction mixture, and about 33% of a phenol solution containing the specific decomposition-reducing additive, or in the case of the comparative examples, the 50 microliter aliquots contained about 67% by volume of a specific reaction mixture, and about 33% of a pure phenol solution. For examples 2–31 the vials were capped and heated to about 150° C. under about 0.1 MPa of air for about 2 hours. For examples 32–41 the vials were capped and heated to about 185° C. in about 15 minutes and held at this temperature for a further 15 minutes under 4.5 MPa of nitrogen. Reaction mixtures for examples 2–41 were analyzed by gas chromatography (GC).

Comparison of appropriate comparative example with the example of the present invention show that the percent decomposition of DPC is lower in those samples in which a decomposition-reducing additive has been added, as compared to equivalent samples which are free of the decomposition-reducing additive.

While the invention has been illustrated and described, it is not intended to be limited to the details shown, since various modifications and substitutions can be made without departing in any way from the spirit of the present invention. For example, reaction mixtures can be heated to different temperatures than those described in the examples listed below. As such, further modifications and equivalents of the invention herein disclosed can occur to persons skilled in the art using no more than routine experimentation, and all such modifications and equivalents are believed to be within the spirit and scope of the invention as defined by the following claims.

TABLE 1

| Example | First Metal (ppm) | Second Metal (eq. vs Pd) | Halide (eq. vs Pd) | Additive (eq. vs Pd) | Initial wt % DPC | % Decomposition of DPC |
|---|---|---|---|---|---|---|
| C1 | Pd(15) | Pb(55) | TEAB (750) | none | 12 | 14.4 |
| 1 | Pd(15) | Pb(55) | TEAB (750) | HBr(1000) | 12 | 1 |

TABLE 2

| Example | First Metal (ppm) | Second Metal (eq. vs Pd) | Third Metal (eq. vs Pd) | Halide (eq. vs Pd) | Base (eq. vs Pd) | Solvent (wt %) | Additive (eq. vs Pd) | Initial wt % DPC | % Decomposition of DPC |
|---|---|---|---|---|---|---|---|---|---|
| C2 | Pd (14) | Pd (105) | Cu (2) | NaBr (790) | NaOH (224) | TG (7) | none | 29.6 | 99 |
| 2 | Pd (14) | Pb (105) | Cu (2) | NaBr (790) | NaOH (224) | TG (7) | HBr (100) | 29.6 | 96 |
| 3 | Pd (14) | Pb (105) | Cu (2) | NaBr (790) | NaOH (224) | TG (7) | EDTA (100) | 29.6 | 81 |
| 4 | Pd (14) | Pb (105) | Cu (2) | NaBr (790) | NaOH (224) | TG (7) | OA (100) | 29.6 | 98 |
| 5 | Pd (14) | Pb (105) | Cu (2) | NaBr (790) | NaOH (224) | TG (7) | NTA (100) | 29.6 | — |
| 6 | Pd (14) | Pb (105) | Cu (2) | NaBr (790) | NaOH (224) | TG (7) | AA (100) | 29.6 | 95 |

TABLE 3

| Example | First Metal (ppm) | Second Metal (eq. vs Pd) | Third Metal (eq. vs Pd) | Halide (eq. vs Pd) | Base (eq. vs Pd) | Solvent (wt %) | Additive (eq. vs Pd) | Initial wt % DPC | % Decomposition of DPC |
|---|---|---|---|---|---|---|---|---|---|
| C7 | Pd (15) | Pd (59) | Ti (2) | NaBr (293) | — | TG (3) | none | 24.4 | 34 |
| 7 | Pd (15) | Pb (59) | Ti (2) | NaBr (293) | — | TG (3) | HBr (100) | 24.4 | 1 |
| 8 | Pd (15) | Pb (59) | Ti (2) | NaBr (293) | — | TG (3) | EDTA (100) | 24.4 | 1 |
| 9 | Pd (15) | Pb (59) | Ti (2) | NaBr (293) | — | TG (3) | OA (100) | 24.4 | 1 |
| 10 | Pd (15) | Pb (59) | Ti (2) | NaBr (293) | — | TG (3) | NTA (100) | 24.4 | 2 |
| 11 | Pd (15) | Pb (59) | Ti (2) | NaBr (293) | — | TG (3) | AA (100) | 24.4 | 16 |
| C12 | Pd (15) | Pb (55) | Ti (2) | NaBr (443) | NaOH (230) | TG (4) | none | 27.4 | 70 |
| 12 | Pd (15) | Pb (55) | Ti (2) | NaBr (443) | NaOH (230) | TG (4) | HBr (100) | 27.4 | 18 |
| 13 | Pd (15) | Pb (55) | Ti (2) | NaBr (443) | NaOH (230) | TG (4) | EDTA (100) | 27.4 | 24 |
| 14 | Pd (15) | Pb (55) | Ti (2) | NaBr (443) | NaOH (230) | TO (4) | OA (100) | 27.4 | 24 |
| 15 | Pd (15) | Pb (55) | Ti (2) | NaBr (443) | NaOH (230) | TG (4) | NTA (100) | 27.4 | 36 |
| 16 | Pd (15) | Pb (55) | Ti (2) | NaBr (443) | NaOH (230) | TG (4) | AA (100) | 27.4 | 60 |

TABLE 3

| Example | First Metal (ppm) | Second Metal (eq. vs Pd) | Third Metal (eq. vs Pd) | Halide (eq. vs Pd) | Base (eq. vs Pd) | Solvent (wt %) | Additive (eq. vs Pd) | Initial wt % DPC | % Decomposition of DPC |
|---|---|---|---|---|---|---|---|---|---|
| C17 | Pd (15) | Cu (7) | Ti (15) | TMAC (790) | NaOH (400) | none | none | 30.8 | 61 |
| 17 | Pd (15) | Cu (7) | Ti (15) | TMAC (790) | NaOH (400) | none | EDTA (100) | 30.8 | 31 |
| 18 | Pd (15) | Cu (7) | Ti (15) | TMAC (790) | NaOH (400) | none | OA (100) | 30.8 | 18 |
| 19 | Pd (15) | Cu (7) | Ti (15) | TMAC (790) | NaOH (400) | none | NTA (100) | 30.8 | 34 |
| 20 | Pd (15) | Cu (7) | Ti (15) | TMAC (790) | NaOH (400) | none | AA (100) | 30.8 | 47 |
| C21 | Pd (15) | Cu (5) | Ti (15) | NaCl (790) | NaOH (363) | TG (5) | none | 20.9 | 91 |
| 21 | Pd (15) | Cu (5) | Ti (15) | NaCl (790) | NaOH (363) | TG (5) | OA (100) | 20.9 | 26 |
| 22 | Pd (15) | Cu (5) | Ti (15) | NaCl (790) | NaOH (363) | TG (5) | NTA (100) | 20.9 | 51 |
| 23 | Pd (15) | Cu (5) | Ti (15) | NaCl (790) | NaOH (363) | TG (5) | AA (100) | 20.9 | 67 |
| C21 | Pd (15) | Cu (5) | Ti (15) | TEAB (780) | NaOH (400) | none | none | 33.3 | 80 |
| 24 | Pd (15) | Cu (5) | Ti (15) | TEAB (780) | NaOH (400) | none | EDTA (100) | 33.3 | 72 |
| 25 | Pd (15) | Cu (5) | Ti (15) | TEAB (780) | NaOH (400) | none | OA (100) | 33.3 | 81 |
| 26 | Pd (15) | Cu (5) | Ti (15) | TEAB (780) | NaOH (400) | none | NTA (100) | 33.3 | 71 |
| 27 | Pd (15) | Cu (5) | Ti (15) | TEAB (780) | NaOH (400) | none | AA (100) | 33.3 | 72 |
| C28 | Pd (15) | Cu (5) | Ti (15) | NaBr (780) | NaOH (400) | TG (7) | none | 32.7 | 93 |
| 28 | Pd (15) | Cu (5) | Ti (15) | NaBr (780) | NaOH (400) | TG (7) | EDTA (100) | 32.7 | 62 |
| 29 | Pd (15) | Cu (5) | Ti (15) | NaBr (780) | NaOH (400) | TG (7) | OA (100) | 32.7 | 81 |
| 30 | Pd (15) | Cu (5) | Ti (15) | NaBr (780) | NaOH (400) | TG (7) | NTA (100) | 32.7 | 84 |
| 31 | Pd (15) | Cu (5) | Ti (15) | NaBr (780) | NaOH (400) | TG (7) | AA (100) | 32.7 | 85 |

TABLE 3

| Example | First Metal (ppm) | Second Metal (eq. vs Pd) | Third Metal (eq. vs Pd) | Halide (eq. vs Pd) | Base (eq. vs Pd) | Solvent (wt %) | Additive (eq. vs Pd) | Initial wt % DPC | % Decomposition of DPC |
|---|---|---|---|---|---|---|---|---|---|
| C32 | Pd (14) | Cu (20) | Ti (27) | NaBr (423) | NaOH (851) | TG (7) | none | 20.5 | 65 |
| 32 | Pd (14) | Cu (20) | Ti (27) | NaBr (423) | NaOH (851) | TG (7) | CA (400) | 20.5 | 5 |
| 33 | Pd (14) | Cu (20) | Ti (27) | NaBr (423) | NaOH (851) | TG (7) | CA (400), HBr (400) | 20.5 | 2 |
| 34 | Pd (14) | Cu (20) | Ti (27) | NaBr (423) | NaOH (851) | TG (7) | CA (400), PA (100) | 20.5 | 4 |
| 35 | Pd (14) | Cu (20) | Ti (27) | NaBr (423) | NaOH (851) | TG (7) | MA (400) | 20.5 | 24 |
| 36 | Pd (14) | Cu (20) | Ti (27) | NaBr (423) | NaOH (851) | TG (7) | SA (600), water (13900) | 20.5 | 8 |
| 37 | Pd (14) | Cu (20) | Ti (27) | NaBr (423) | NaOH (851) | TG (7) | OA (400), | 20.5 | 3 |

TABLE 3-continued

| Example | First Metal (ppm) | Second Metal (eq. vs Pd) | Third Metal (eq. vs Pd) | Halide (eq. vs Pd) | Base (eq. vs Pd) | Solvent (wt %) | Additive (eq. vs Pd) | Initial wt % DPC | % Decomposition of DPC |
|---|---|---|---|---|---|---|---|---|---|
| C38 | Pd (15) | Pb (51) | Ti (2) | NaBr (391) | NaOH (109) | TG (7) water (13900) none | 18.0 | 41 |
| 38 | Pd (15) | Pb (51) | Ti (2) | NaBr (391) | NaOH (109) | TG (7) | EDTA (400) | 18.0 | 4 |
| 39 | Pd (15) | Pb (51) | Ti (2) | NaBr (391) | NaOH (109) | TG (7) | MA (400) | 18.0 | 11 |
| 40 | Pd (15) | Pb (51) | Ti (2) | NaBr (391) | NaOH (109) | TG (7) | PA (400) | 18.0 | 6 |
| 41 | Pd (15) | Pb (51) | Ti (2) | NaBr (391) | NaOH (109) | TG (7) | CA (400) | 18.0 | 5 |

What is claimed is:

1. A method for reducing the percent decomposition of an aromatic carbonate in a first reaction mixture comprising said aromatic carbonate, at least one first metal source selected from the group consisting of a Group 8 metal source, a Group 9 metal source and a Group 10 metal source; and at least one second metal source selected from the group consisting of a Group 11 metal source and a Group 14 metal source, the method comprising the step of adding at least one decomposition-reducing additive to said first reaction mixture so as to produce a second reaction mixture in which the percent of said aromatic carbonate present in said second reaction mixture after a predetermined amount of time is greater than the percent of said aromatic carbonate that would be present in the first reaction mixture in the absence of adding the decomposition-reducing additive, after the same predetermined amount of time.

2. The method of claim 1, wherein said first reaction mixture further comprises at least one member selected from the group consisting of an aromatic hydroxy compound, an aryloxide salt, water, a salt, an organic solvent, a base source, and any mixtures thereof.

3. The method of claim 2, wherein the decomposition-reducing additive comprises at least one member selected from the group consisting of a compound comprising at least one chelating functionality, a protic acid, and any mixtures thereof.

4. The method of claim 3, wherein the chelating functionality comprises at least one carboxylate functionality.

5. The method of claim 4, wherein the decomposition-reducing additive is at least one member selected from the group consisting of oxalic acid, adipic acid, nitrilotriacetic acid, ethylenediaminetetraacetic acid, citric acid, succinic acid, malonic acid, hydrobromic acid, phosphoric acid, and any mixtures thereof.

6. The method of claim 1, wherein the first metal source is a palladium source.

7. The method of claim 1, wherein the second metal source is one member selected from the group consisting of a copper source and a lead source.

8. The method of claim 7, wherein the first reaction mixture further comprises a third metal source.

9. The method of claim 8, wherein the third metal source is a Group 4 metal source.

10. The method of claim 9, wherein the third metal source is a titanium source.

11. The method of claim 1, wherein the second metal source is a Group 11 metal source, and the first reaction mixture further comprises a third metal source which is a Group 14 metal source.

12. The method of claim 11, wherein the second metal source is a copper source, and the third metal source is a lead source.

13. The method of claim 1, wherein the second metal source is a Group 14 metal source and wherein the decomposition-reducing additive is a protic acid source.

14. A method for reducing the percent decomposition of an aromatic carbonate in a first reaction mixture comprising said aromatic carbonate, a palladium source, a lead source, and at least one member selected from the group consisting of an aromatic hydroxy compound, an aryloxide salt, water, a salt, an organic solvent, a base source, and any mixtures thereof, the method comprising the step of adding at least one member selected from the group consisting of hydrobromic acid and phosphoric acid to said first reaction mixture, so as to produce a second reaction mixture in which the percent of said aromatic carbonate present in said second reaction mixture after a predetermined amount of time is greater than the percent of said aromatic carbonate that would be present in the first reaction mixture in the absence of adding the decomposition-reducing additive, after the same predetermined amount of time.

15. A method for reducing the percent decomposition of an aromatic carbonate in a first reaction mixture comprising said aromatic carbonate, a palladium source, a copper source, a titanium source, and at least one member selected from the group consisting of an aromatic hydroxy compound, an aryloxide salt, water, a salt, an organic solvent, a base source, and any mixtures thereof, the method comprising the step of adding at least one member selected from the group consisting of oxalic acid, adipic acid, nitrilotriacetic acid, ethylenediaminetetraacetic acid, citric acid, succinic acid, malonic, hydrobromic acid, phosphoric acid, and any mixtures thereof to said first reaction mixture, so as to produce a second reaction mixture in which the percent of said aromatic carbonate present in said second reaction mixture after a predetermined amount of time is greater than the percent of said aromatic carbonate that would be present in the first reaction mixture in the absence of adding the decomposition-reducing additive, after the same predetermined amount of time.

16. A method for reducing the percent decomposition of an aromatic carbonate in a first reaction mixture comprising said aromatic carbonate, a palladium source, a lead source, and at least one member selected from the group consisting of an aromatic hydroxy compound, an aryloxide salt, water, a salt, an organic solvent, a base source, and any mixtures thereof, the method comprising the step of adding at least one member selected from the group consisting of hydrobromic acid, phosphoric acid, oxalic acid, adipic acid, nitrilotriacetic acid, ethylenediaminetetraacetic acid, citric acid, succinic acid, malonic acid, hydrobromic acid, phosphoric acid, and any mixtures thereof to said first reaction mixture, so as to produce a second reaction mixture in which the percent of said aromatic carbonate present in said second reaction mixture after a predetermined amount of time is greater than the percent of said aromatic carbonate that would be present in the first reaction mixture in the absence of adding the decomposition-reducing additive, after the same predetermined amount of time.

17. The method of claim 16, wherein the first reaction mixture further comprises a titanium source.

18. The method of claim 14, wherein the temperature of said first reaction mixtures is between about 50° C. and about 220° C., and the temperature of said second reaction mixture is between about 50° C. and about 220° C.

19. The method of claim 15, wherein the temperature of said first reaction mixtures is between about 50° C. and about 220° C., and the temperature of said second reaction mixture is between about 50° C. and about 220° C.

20. The method of claim 16, wherein the temperature of said first reaction mixtures is between about 50° C. and about 220° C., and the temperature of said second reaction mixture is between about 50° C. and about 220° C.

21. The method of claim 17, wherein the temperature of said first reaction mixtures is between about 50° C. and about 220° C., and the temperature of said second reaction mixture is between about 50° C. and about 220° C.

22. The method of claim 2, wherein the temperature of said first reaction mixtures is between about 50° C. and about 220° C., and the temperature of said second reaction mixture is between about 50° C. and about 220° C.

23. The method of claim 14, wherein the pressure of said first reaction mixtures is between about $1.3 \times 10^{-4}$ MPa and about 10 MPa, and the pressure of said second reaction mixture is between about $1.3 \times 10^{-4}$ MPa and about 10 MPa.

24. The method of claim 15, wherein the pressure of said first reaction mixtures is between about $1.3 \times 10^{-4}$ MPa and about 10 MPa, and the pressure of said second reaction mixture is between about $1.3 \times 10^{-4}$ MPa and about 10 MPa.

25. The method of claim 16, wherein the pressure of said first reaction mixtures is between about $1.3 \times 10^{-4}$ MPa and about 10 MPa, and the pressure of said second reaction mixture is between about $1.3 \times 10^{-4}$ MPa and about 10 MPa.

26. The method of claim 17, wherein the pressure of said first reaction mixtures is between about $1.3 \times 10^{-4}$ MPa and about 10 MPa, and the pressure of said second reaction mixture is between about $1.3 \times 10^{-4}$ MPa and about 10 MPa.

27. The method of claim 2, wherein the pressure of said first reaction mixtures is between about $1.3 \times 10^{-4}$ MPa and about 10 MPa, and the pressure of said second reaction mixture is between about $1.3 \times 10^{-4}$ MPa and about 10 MPa.

* * * * *